(12) United States Patent
Gupta

(10) Patent No.: US 8,987,481 B1
(45) Date of Patent: Mar. 24, 2015

(54) METHOD FOR ISOLATION OF BULK ANTHOCYANIDINS AND OTHER BIOACTIVES

(71) Applicant: Ramesh C Gupta, Prospect, KY (US)

(72) Inventor: Ramesh C Gupta, Prospect, KY (US)

(*) Notice: Subject to any disclaimer, the term of this patent is extended or adjusted under 35 U.S.C. 154(b) by 0 days.

(21) Appl. No.: 14/187,245

(22) Filed: Feb. 22, 2014

Related U.S. Application Data

(60) Provisional application No. 61/768,509, filed on Feb. 24, 2013.

(51) Int. Cl.
*C07D 311/76* (2006.01)
*A23L 1/275* (2006.01)

(52) U.S. Cl.
CPC .............. *C07D 311/76* (2013.01); *A23L 1/2751* (2013.01)
USPC ........................................................ 549/406

(58) Field of Classification Search
CPC .............................. C07D 311/76; A23L 1/2751
USPC ........................................................ 549/406
See application file for complete search history.

(56) References Cited

U.S. PATENT DOCUMENTS

| | | | |
|---|---|---|---|
| 3,266,903 A | 8/1966 | Jurd | |
| 4,208,434 A | 6/1980 | Iacobucci et al. | |
| 4,481,226 A | 11/1984 | Crosby et al. | |
| 7,211,413 B2 | 5/2007 | Matsumoto et al. | |
| 8,017,162 B2 | 9/2011 | Shimoda et al. | |

OTHER PUBLICATIONS

Noda et al. (J. Agric. Food Chem. 2002, 50, 166-171).*
Forsyth, W. G. C.; Simmonds, N. W. (Nature (1957), 180, p. 247).*

* cited by examiner

*Primary Examiner* — Kristin Vajda
*Assistant Examiner* — Valerie Rodriguez-Garcia
(74) *Attorney, Agent, or Firm* — Joan L. Simunic

(57) ABSTRACT

This invention describes a simple, rapid and cost-effective method to isolate bulk quantities of relatively pure and enriched anthocyanidins and other plant bioactives. The method is based on the principle of solubility. Some bioactives (anthocyanidins) were extracted in an aqueous solvent, transferred to a non-aqueous solvent and finally insolubilized by adding a miscible solvent in which the bioactive was insoluble. Thus, anthocyanidins were isolated from anthocyanin-enriched berries or non-enriched, dark-colored fruits, vegetables and grains by extraction of anthocyanins, acid hydrolysis, and extraction of the resulting anthocyanidins, followed by their insolubilization (precipitation). Some bioactives (hydrophobic and hydrophilic) were extracted in a solvent with high solubility and then directly insolubilized by adding a miscible solvent in which the bioactive was insoluble, for example, withaferin A from enriched *Withania somnifera* and punicalagins from enriched *punica* extract.

9 Claims, No Drawings

METHOD FOR ISOLATION OF BULK ANTHOCYANIDINS AND OTHER BIOACTIVES

CROSS-REFERENCE TO PRIOR APPLICATIONS

The present application claims priority to U.S. Patent Application 61/768,509 filed Feb. 24, 2013, which is incorporated by reference in its entirety.

BACKGROUND

Colors have played a vital role in human life—be it beverages, foods, cosmetics, prescription drugs, etc. While plant sources for natural colors have been known for a long time, synthetic colors have predominated in the human environment all along largely because of cost effectiveness. In the past decade or so, there has been increasing interest in the use of natural colors instead of synthetic colors in beverages and the food chain in order to eliminate potential adverse effects associated with synthetic compounds. A major surge in natural colors seems to emerge from recent reports that anthocyanidins (anthos)/anthocyanins from berries are protective against various cancers, aid in reversal of memory loss, are anti-diabetic, and protective against cardiovascular disease. For example, recent studies have shown synergistic anti-tumor activity of a native mixture of anthos isolated from bilberry against human lung cancer xenograft in nude mice. Anti-cancer activity of anthos/anthocyanins is implicated against breast cancer, colon cancer and esophageal cancer based on various cell culture and/or in vivo studies. Native anthos isolated from bilberry, a European 'cousin' of blueberry, also showed dose-dependent kill of human pancreatic cancer cells in cell culture.

Anthocyanins are anthos conjugated to a variety of sugars (glucosides, arabinosides, etc.—as mono-, di- and tricyclic). While over 500 anthocyanins are reported, most of them are derivatives of six major anthos, namely, delphinidin (Dp), cyanidin (Cy), peonidin (Pe), petunidin (Pt), malvidin (Mv) and pelargonidin (Pg). These anthos are structural analogs, and are present in different berries (e.g., blueberry, blackberry, black raspberry, strawberry, cranberry), and other dark-colored fruits (e.g., red and black grapes, plums), vegetables (e.g., purple cabbage, purple potatoes, purple sweet potatoes, purple corn) and grains (e.g., black beans, black lentils, black soy beans, black rice). However, the classical methods to isolate anthos are cumbersome and time consuming, requiring days and weeks for their isolation, and are not economical for commercial production.

Research efforts are being directed toward the isolation of anthos/anthocyanins in bulk quantities. The Research Foundation of the State University of New York (SUNY Buffalo) developed a fermentation process to produce anthocyanins and anthocyanidins. Researchers at the Rutgers University have reported a process in which soy protein isolates capture anthocyanins from dark-colored fruits juices. The products resulting from these technologies are, however, as yet unavailable in the open market and their commercial aspects, costs and generality of their technologies remain to be determined.

The purpose of this development is to report a simple, rapid and cost-effective and scalable method for isolation of pure anthos and other plant bioactives. The method reported here is based on the principle of solubility in specific solvents to isolate large quantities of anthos and other plant bioactives.

SUMMARY OF THE INVENTION

The present development is a simple, rapid, cost-effective and scalable procedure for isolation of relatively pure and enriched anthocyanidins from various dark-colored berries, grapes, vegetables and grains. The initial method was developed using commercially available anthocyanin-enriched bilberry, black currant, and elderberry. The method was then adapted to non-enriched, dark-colored fruits, vegetables and grains.

DETAILED DESCRIPTION OF THE PREFERRED EMBODIMENT

The following description is intended to provide the reader with a better understanding of the invention. The description is not intended to be limiting with respect to any element not otherwise limited within the claims.

The present development is a simple, rapid and cost-effective method for bulk isolation of anthos from dark-colored natural sources, such as fruits, vegetables and grains. The process comprising the steps of obtaining an anthocyanin-containing material, dissolving the anthocyanin-containing material in an acidic solution, converting the anthocyanin-containing material to an anthocyanidin-containing material with heat, extracting the anthocyanidin-containing material into a polar solvent, and, then combining the anthocyanidin-containing polar solvent with a non-polar solvent to precipitate the anthocyanidins or anthos.

The six known major anthocyanidins or anthos (Dp, Cy, Pe, Pt, My and Pg) can be isolated in large quantities either individually (Dp, Cy, Pg) or as the predominant species (Pt, Pe, Mv). Source materials for these anthos are available in abundance. Exemplary sources for the anthocyanidin-containing material include bilberry, blueberry, jamun, black currant, elderberry (Cy), chokeberry (Cy), blueberry, black grape skin (Mv), purple potatoes (Pt), purple sweet potatoes (Pe), melon radish (Pg), pink radish skin (Pg), eggplant skin (Dp), black beans, black lentils, and black soy beans. Bilberry, elderberry, black currant, elderberry and chokeberry are available in enriched form with 20-36% anthocyanin contents, thus requiring lesser quantities of the source material to produce large quantities of anthos. Anthocyanin-enriched purple potatoes, purple sweet potatoes, purple corn, cranberry and black bean husk are also commercially available.

The polar solvent may be any polar organic solvent, such as a higher-chain alcohol or tetrahydrofuran. Exemplary higher-chain alcohols include isobutanol, isoamylalcohol, tertiary amylalcohol, 1-pentanol, 1-hexanol, 1-heptanol, 1-octanol and 1-docenol. In a preferred embodiment, the polar solvent is selected from the group consisting of isoamyl alcohol, 1-pentanol, 1-hexanol and 1-heptanol.

The non-polar solvent may be any food-grade non-polar organic solvent. In a preferred embodiment, the non-polar solvent is petroleum ether. The test bioactives are insoluble in the presence of petroleum ether, which generally results in high purity and recovery. The material collected following drying under vacuum is porous, flaky/crystalline, further adding to scalability of the method.

Unless defined otherwise, all technical and scientific terms used herein have the same meaning as commonly understood by one of ordinary skill in the art to which the presently disclosed subject matter pertains. Representative methods, devices, and materials are described herein, but are not intended to be limiting unless so noted.

The terms "a", "an", and "the" refer to "one or more" when used in the subject specification, including the claims. Thus, for example, reference to "an extraction" includes a plurality of such extractions, and so forth.

Unless otherwise indicated, all numbers expressing quantities of components, conditions, and otherwise used in the specification and claims are to be understood as being modified in all instances by the term "about". Accordingly, unless indicated to the contrary, the numerical parameters set forth in the instant specification and attached claims are approximations that can vary depending upon the desired properties sought to be obtained by the presently disclosed subject matter As used herein, the term "about", when referring to a value or to an amount of mass, weight, time, volume, concentration, or percentage can encompass variations of, in some embodiments ±20%, in some embodiments ±10%, in some embodiments ±5%, in some embodiments ±1%, in some embodiments ±0.5%, and in some embodiments to ±0.1%, from the specified amount, as such variations are appropriate in the disclosed application.

All compositional percentages used herein are presented on a "by weight" basis, unless designated otherwise.

The following are representative examples for isolation of relatively pure anthos from natural food sources using the process of the present development. These examples are presented to further explain the invention and are not intended, or to be taken, to limit the scope of the invention. For the purpose of this writing, any reference to "ambient temperature" refers to surrounding air temperatures of about 50° F. to about 110° F.

Anthocyanidins from enriched bilberry. Bilberry, blueberry and jamun (*Syzygium cumini* L, Indian blackberry) all contain glycosides of five anthos, namely, Dp, Cy, Pe, Pt and Mv, in different compositions based on the type of berries. In an exemplary embodiment, not intended to limit the scope of the development, an anthocyanidin-containing material is dissolved in acidic solution, and then extracted into a polar solvent. Preferred polar solvents include, but are not limited to, higher-chain alcohols, such as, isobutanol, isoamylalcohol, tertiary amylalcohol, 1-pentanol, 1-hexanol, 1-heptanol, 1-octanol and 1-docenol. Anthos are extracted with maximum efficiency in isoamylalcohol, 1-pentanol, 1-hexanol and 1-heptanol. The highest extraction was found in 1-pentenol and the least in 1-docenol. The anthos-containing polar solvent is then combined with a non-polar solvent to precipitate the material as crystals/flakes. An exemplary non-polar solvent is petroleum ether due to its easy availability and relatively low cost. The resulting crystals have a purity of greater than about 80%, with greater than about 40% recovery compared to theoretical yield.

Example 1

About 50 g of bilberry powder containing 36% anthocyanins, which contains about 25% anthos, is dissolved in 6 L of 3N HCl using a sonicator at 47° C. (Bransonic Ultrasonic Cleaner, Branson). The solution is heated for about 60 min after the temperature has reached around 90° C. in order to hydrolyze anthocyanins to anthocyanidins. The solution is then cooled in ice, and filtered through Whatman No. 3 paper using a Buchner funnel. The resulting anthos components are selectively extracted in depleted volumes of 1-pentanol. The first extraction is with 0.1 volume of 1-pentanol, followed sequentially by extractions using 0.1, 0.05 and 0.05 volume of 1-pentanol, respectively, for complete recovery. The pooled pentanol phase is back-extracted with 0.05 volume of 0.1% HCl to remove any residual sugars. The solution is finally mixed with 1.2-1.5 volume of petroleum ether. The anthos precipitate is allowed to settle under gravity, the bottom phase is collected and washed with petroleum ether. The precipitate is poured in a glass petri dish and dried under vacuum. This process results in crystals/flakes of anthos. Analysis of the isolated anthos precipitate by 1-directional PEI-cellulose TLC and HPLC shows the presence of five anthos components, consistent with the chromatographic property of Dp, Cy, Pe, Pt and Mv. The purity of this material is assessed by HPLC to be nearly 84% by comparison with cyanidin-3-glucoside with a yield of about 4.7 g anthos per 50 g of 36% anthocyanin-enriched bilberry, or about a 45% yield compared to theoretical yield.

Example 2A

The method of Example 1 is followed, except the purity of the isolated anthos is about 88% with a yield of about 4.8 g anthos per 50 g enriched bilberry, or about a 50% yield compared to theoretical yield.

Example 2B

The method of Example 1 is followed, except the bilberry extract contains about 25% anthocyanins (or about 16.6% anthos), and the purity of the isolated anthos is over 85%, with about 58% recovery compared to the expected value.

Example 3

Anthos isolated from billberry according to Example 1 is further purified by dissolving about 200 mg isolated anthos in 0.1% HCl, loading onto a 10 g-C18 cartridge and eluting with acidified ethanol. The recovered anthos are found to be about 95% pure as assessed by HPLC.

Anthocyanidins from Enriched Black Currant.

Black currant contains glycosides of exclusively two anthos, namely, Dp and Cy. When enriched black currant powder (50 g), containing 30% anthocyanins (about 20% anthos), is processed according to the conditions of Example 1, it produces two anthos, Dp and Cy, as determined by PEI-cellulose TLC and HPLC. The purity of the isolated anthos is about 89% based on HPLC comparison with cyanidin-3-glycoside.

Anthocyanidins from Enriched Elderberry and Chokeberry Extracts.

Elderberry and chokeberry both contain glycosides of almost exclusively one anthocyanidin, Cy. Extraction of enriched elderberry powder (50 g), containing 25% anthocyanins (about 17.5% anthos), under the conditions of Example 1, it produces almost exclusively Cy, as determined by 1-directional PEI-cellulose TLC and HPLC. Similar results are obtained from 20% anthocyanin-enriched chokeberry.

Anthocyanidins from Enriched Purple Corn Extracts.

Purple corn contains glycosides of almost exclusively one anthocyanidin, Cy. Extraction of enriched purple corn powder (50 g), containing 7.5% anthocyanins (2.5 g expected anthos), under the conditions of Example 1, it produces almost exclusively Cy, as determined by 1-directional PEI-cellulose TLC and HPLC. The isolated anthos is about 85% pure, with a yield of 0.82 g from 50 g enriched material, which is about 33% of the expected recovery.

Anthocyanidins from Red Grape Juice Extract.

Red (black) grape juice extract contains glycosides of My as a major anthocyanidin along with Cy and Pe as minor components. Extraction of enriched red grape juice extract powder (100 g), containing 24% anthocyanins (about 16% anthos), under the conditions of Example 1, it produces predominantly My along with Cy and Pe, as determined by 1-directional PEI-cellulose TLC. The isolated anthos are over 80% pure, with a yield of 2.35 g from 100 g enriched material, which is about 15% of the expected recovery.

Isolation of Anthocyanidins from Blueberry.

Blueberry is known to contain glycosides of five anthocyanidins (Dp, Cy, Pe, Pt and Mv). About 50 g of powdered blueberry containing 1.4% anthocyanins (equivalent to about 1% anthos) is extracted with about 250 ml ethanol containing 0.2% HCl. The extraction is performed in an ultrasonicator (Bransonic Ultrasonic Cleaners, Branson) at about 47° C. The supernatant is collected by centrifugation, and the sediment is extracted three more times. The pooled extract is concentrated to a small volume (about 20 ml) using a rotavapor. This solution is diluted to 200-300 ml with 3.3N HCl, hydrolyzed to anthos and recovered by 1-pentanol extraction and recovered by precipitation with petroleum ether as described previously, except that the pentanol extract is concentrated first in the rotavapor to increase the anthos concentration. Analysis by PEI-cellulose TLC and HPLC show the presence of the expected five anthos (Dp, Cy, Pe, Pt and Mv). HPLC analysis indicates the enrichment of the recovered anthos is much higher than the original material.

Isolation of Anthocyanidins from Black Grape Skin.

Black grape skin contains glycosides of four anthos (Cy, Pe, Pt and Mv). The same procedure as used to isolate anthos from blueberry is followed except the anthos source is black grape skin. Analysis by PEI-cellulose TLC and HPLC show the presence of the expected four anthos (Mv, Cy, Pe and Pt). HPLC analysis shows that purity and enrichment of the recovered anthos is much higher than the original material.

Isolation of Anthocyanidins from Purple Potatoes.

Purple potato is known to contain glycosides of four anthos (Pe, Pt, My and Pg). About 50 g of powdered purple potato is extracted in acidified ethanol four times using an ultrasonicator at about 47° C. for about 45 min. Following centrifugation, the material is re-extracted twice for 30 min each. The pooled supernatant is concentrated to about 20 ml, diluted to 200 ml 3.3 N HCl, heated at 90° C. for 60 min and filtered through Whatman No. 3 paper. The solution is mixed with about 2 volume of petroleum ether and the resulting precipitate is dried under vacuum. Analysis by PEI-cellulose TLC shows the presence of four anthos (Pt, Pe, My and Pg), which is further confirmed by HPLC. HPLC analysis also shows the purity and enrichment of the isolated anthos are significantly increased compared to the original material.

In another preparation, dried pieces of purple potatoes (50 g) were extracted directly in 300 ml of 3N HCl as described above. Following decanting, the material was re-extracted twice for 30 min each. The pooled extract was heated at 90° C. for 60, min, cooled, and filtered through Whatmen No. 3 paper. Following concentration with rotavapor to about 50 ml, the solution was extracted with 1-pentanol thrice and anthos were precipitated with petroleum ether as described above, except it required higher volumes. Analysis by HPLC showed enrichment of the anthos compared to the original material. Upon further purification with C18 cartridge, the purity increased further. This method further expedited the procedure with similar purity and recovery of the anthos as obtained by extracting the potato powder with ethanol.

Isolation of Anthocyanidins from Purple Sweet Potatoes.

Purple sweet potato contains glycosides of two anthos (Pe and Cy). The same procedure as used to isolate anthos from purple potato is followed except the anthos source is purple sweet potato. Analysis by PEI-cellulose TLC and HPLC show the presence of the expected two anthos (Cy and Pe). HPLC analysis shows enrichment of the anthos compared to the original material.

Isolation of Anthocyanidins from Melon Radish and Pink Radish Skin.

Radish is known to contain glycosides of only one antho, Pg. About 50 g melon radish powder is processed essentially as described above for purple potatoes. The ethanol extract is reduced to small volume (about 20 ml) and diluted to 3N HCl and then hydrolyzed to anthos as described above for grape skin. Analysis of the isolated anthos by 1-directional PEI-cellulose TLC shows only one antho spot, identified as Pg. The purity was increased by passage through a C18 cartridge. Powder of pink radish skin processed essentially as above resulted higher purity and recovery of Pg than melon radish.

Isolation of Anthocyanidins from Eggplant Skin.

Eggplant skin is known to contain glycosides of only one antho, Dp. About 50 g eggplant skin powder is processed essentially as described above for purple potatoes, except that the pooled and concentrated ethanol extract of eggplant skin failed to provide any precipitate when mixed with petroleum ether. The ethanol extract is reduced to small volume (about 20 ml) and diluted to 3N HCl and then hydrolyzed to anthos as described above for grape skin. Analysis of the isolated anthos by 1-directional PEI-cellulose TLC shows only one antho spot, identified as Dp. HPLC analysis showed significant enrichment of Dp. The purity was increased by passage through a C18 cartridge.

Isolation of Anthos from Black Beans, Black Lentils and Black Soy Beans.

Whole black beans (100 g) were extracted in 300 ml 3N HCl at 47° C. using ultrasonication for 45 min. After decanting the supernatant, the beans were re-extracted twice for 30 min each. The pooled extract was heated at 90° C. for 60 min, cooled, and filtered through Whatman No. 3 paper. The solution was extracted with 1-pentanol, concentrated by rotavapor and the anthos were insolubilized by the addition of petroleum ether. Analysis of the isolated anthos by HPLC and by 1-directional PEI-cellulose TLC showed the presence of three spots which were identified as Dp, Pt and My. HPLC analysis showed significant enrichment of the anthos. The purity of the anthos was further improved by passage through a C18 cartridge. Following the same procedure, black lentils and black soy beans also resulted in three anthos, namely, Dp, Pt and My in highly enriched form. However, the anthos yields from black lentils and black soy beans were several fold lower than black beans.

Anthocyanidins from Hibiscus Flowers.

Hibiscus contains glycosides of predominantly Dp together with Cy and Pe and My as minor components. Dried flowers were extracted with 5 vol of 3N HCl using sonicator at 47° C. for 45 min. The extraction was repeated two more times with 3 vol each of HCl. The pooled extract was hydrolyzed at 90° C. for 60 min and cooled in ice. The anthos were extracted in 1-pentanol and insolubilized with petroleum ether and dried. Extraction of the dried flowers under the above conditions produces predominantly Dp along with Cy, Pe and Mv, as determined by 1-directional PEI-cellulose TLC. The isolated anthos was over 40% pure, with a yield of 0.71 g from 100 g dried flowers.

Storage and Stabilization of Anthocyanidins.

The isolated anthos are stable when stored in amber bottles under argon at −20° C. Both anthos and anthocyanins are highly unstable in solution form. However, when bound to cellulose, these compounds can be stabilized for a long period of time. Edible cellulose formulations that are used routinely in beverage and food industries are commercially available. Therefore, anthos isolated by the method described here can be readily stabilized with edible cellulose or pectin or other edible materials and used in beverages and foods to provide natural colors, as well as used as nutraceuticals and provide health benefits due to known antioxidant, antiproliferative and anticancer activities of anthos.

Isolation of Punicalagins from Enriched *Punica* Husk.

Punicalagins are known for their potent antioxidant activity. To determine the generality of the method developed for isolation of anthos, we determined if punicalagins present in enriched *punica* husk (30% punacalagins) could be purified by this simple, rapid and cost-effective procedure. The enriched *punica* extract powder (40 g) was dissolved in ethanol which was then mixed with 1.5 volumes of petroleum ether to insolubilize punicalagins. The proportion of petroleum ether was predetermined for optimal purity and recovery of punicalagins by adding 0.8, 1, 1.2, 1.5 and 2 volume of petroleum ether. Punicalagins precipitate was dried under vacuum which resulted in a porous/flaky material, with nearly 80% purity.

Isolation of withaferin A from *Withania sominifera*.

Withaferin A, a triterpinoid isolated from the Ayurvedic herb "ashwagandha" is gaining a lot of attention lately because of its high therapeutic potential against various cancers, such as pancreas cancer, breast cancer, prostate cancer, uterine cervical cancer and lung cancer, angiogenesis, ALS (a progressive neurodegenerative disease), among others. Despite its therapeutic potential, no clinical studies have been reported with this compound because of its unavailability in sufficient quantities and high costs.

To determine if the method of the present invention can purify withaferin A, 2.4% withaferin A-containing *Withania somenifera* extract (500 g) was extracted with 5 volumes of tetrahydrofuran at 47° C. for 1 h using ultrasonication (Bransonic ultrasonication Cleaners, Branson). Following centrifugation, the supernatant was collected and the sediment was re-extracted with 3 volumes of tetrahydrofuran for 30 min. These extraction conditions provided almost complete recovery of withaferin A compared to the expected value, based on HPLC analysis. The pooled extract was concentrated by 7-8 times by rotavapor and then precipitated with 3.3 volumes of petroleum ether; the optimal amount of petroleum ether was predetermined by adding 1, 1.5, 2, 2.5, 3 and 3.5 volume of petroleum ether. Analysis of the lyophilized precipitate by HPLC showed about 18% purity, with over 90% recovery, based on HPLC analysis. This extract is further extracted twice with 8 volumes and 4 volumes of dichloroform. The pooled extract is concentrated with rotavapor and finally dried under vacuum. The dichloromethane extract was still contaminated with green impurities (chlorophyll) and was about 34% purity with over 90% recovery compared with the original material based on HPLC analysis. The green impurity was removed substantially by dissolving the extract in ethanol:acetonitrile (1:1) and treating with activated charcoal. The charcoal treatment further impured the purity to 38-40%, without any significant loss occurring in this purification step. Thus, the starting material with 2.4% withaferin A can be rapidly converted to 40% withaferin A-enriched extract, with over 80% recovery.

In another preparation, 30% withaferin A-containing *Withania somenifera* extract (5 g) was extracted with tetrahydrofuran and then precipitated with 3 volumes of petroleum ether. Analysis of the lyophilized precipitate showed that the material was 62% pure. These data suggest that extractions with tetrahydrofuran and petroleum ether can rapidly and significantly improve the purity of withaferin A.

An unexpected benefit of the present development is the relative simplicity and ease by which anthos can be isolated from naturally occurring sources. This isolation can be achieved using food grade solvents for extraction thereby delivering a material which can be used as a colorant in edible products.

It is anticipated that other sources of anthocyanidins may be used to derive anthos according to the method set forth herein. Specific measurements relevant to the process are provided herein for the purpose of demonstrating the invention, but these measurements are not intended to limit the scope of the invention. It is understood that one skilled in the art may make alterations to the embodiments shown and described herein without departing from the scope of the invention.

What is claimed is:

1. A process for the isolation of anthocyanidins from natural sources, the process comprising the steps:
   a. obtaining an anthocyanin-containing material;
   b. dissolving said anthocyanin-containing material in an acidic solution;
   c. heating the anthocyanin-containing acidic solution to convert anthocyanins to anthocyanidins;
   d. extracting said anthocyanidins into a polar solvent;
   e. combining the anthocyanidin-containing polar solvent with up to 3.3 volumes of a non-polar solvent to precipitate the anthocyanidins; and,
   f. isolating and collecting said anthocyanidin precipitate from the non-polar solvent by sedimentation; wherein the non-polar solvent is petroleum ether.

2. The process of claim 1 wherein said anthocyanin-containing material is selected from the group consisting of bilberry, blueberry, jamun, black currant, elderberry, chokeberry, blueberry, black grape skin, purple potatoes, purple sweet potatoes, melon radish, pink radish skin, eggplant skin, black beans, black lentils, and black soy beans.

3. The process of claim 1 wherein said acidic solution comprises aqueous hydrochloric acid.

4. The process of claim 3 wherein said acidic solution comprises ethanol and aqueous hydrochloric acid.

5. The process of claim 1 wherein said polar solvent is an alcohol or tetrahydrofuran.

6. The process of claim 5 wherein said polar solvent is selected from the group consisting of isobutanol, isoamylalcohol, tertiary amylalcohol, 1-pentanol, 1-hexanol, 1-heptanol, 1-octanol, 1-docenol, and tetrahydrofuran.

7. The process of claim 6 wherein said polar solvent is selected from the group consisting of isoamyl alcohol, 1-pentanol, 1-hexanol and 1-heptanol.

8. The process of claim 1 further comprising a step of drying said anthocyanidin precipitate after step (f).

9. The process of claim 1 wherein an ultrasonicator is used to perform the extraction of step (d).

* * * * *